Figure 1:
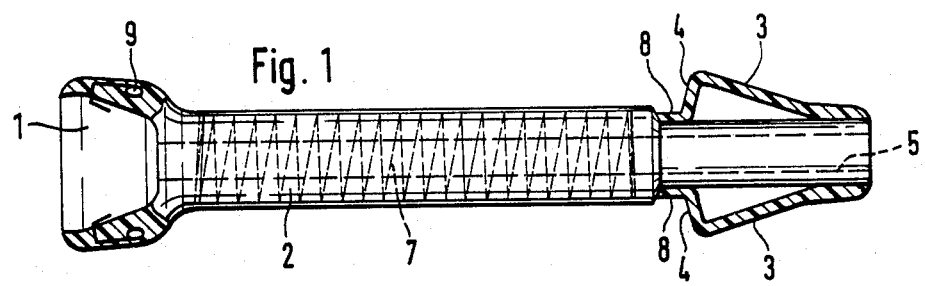

United States Patent [19]

Koss

[11] Patent Number: 4,825,861
[45] Date of Patent: May 2, 1989

[54] ENDOTUBE

[75] Inventor: Walter Koss, Geisenheim, Fed. Rep. of Germany

[73] Assignee: Walter Koss of Industriestrasse, Geisenheim, Fed. Rep. of Germany

[21] Appl. No.: 5,438
[22] PCT Filed: May 2, 1986
[86] PCT No.: PCT/EP86/00263
§ 371 Date: Jan. 5, 1987
§ 102(e) Date: Jan. 5, 1987
[87] PCT Pub. No.: WO86/06616
PCT Pub. Date: Nov. 20, 1986

[30] Foreign Application Priority Data

May 4, 1985 [DE] Fed. Rep. of Germany ... 8513185[U]

[51] Int. Cl.$^4$ .............................................. A61M 25/00
[52] U.S. Cl. .................. 128/207.14; 128/200.26; 623/9
[58] Field of Search .......... 623/9; 128/200.26, 207.14, 128/207.15, 207.16, 757; 604/104, 105, 106, 107, 108, 109, 280, 287, 1

[56] References Cited

U.S. PATENT DOCUMENTS

| 3,807,408 | 4/1974 | Summers | 604/104 |
| 3,896,804 | 7/1975 | Ekbladh | 604/280 |
| 4,043,338 | 8/1977 | Homm | 128/207.15 |
| 4,141,364 | 2/1979 | Schultze | 128/207.15 |
| 4,614,516 | 9/1986 | Blom | 623/9 |

FOREIGN PATENT DOCUMENTS

| 138089 | 9/1984 | European Pat. Off. . |
| 125754 | 4/1919 | United Kingdom | 128/357 |
| 1518654 | 7/1978 | United Kingdom . |

Primary Examiner—Richard J. Apley
Assistant Examiner—James Prizant
Attorney, Agent, or Firm—Gifford, Groh, Sheridan, Sprinkle and Dolgorukov

[57] ABSTRACT

Described is an endotube for positioning in particular in the esophagus, which at one end has a funnel-like enlargement portion (1), a tubular central portion (2) and at the other end a thickened portion which enlarges towards the central portion and which after having passed through a constriction makes it difficult to withdraw the endotube. The thickened portion is formed from two hollow thin-walled limb portions (3) which are open to the interior of the central portion (2) and which project out of the central portion (2) and which rise in a ramp-like configuration towards the central portion and which then terminate with a steep drop (4). By virtue of that configuration the limbs (3) can be fully folded in, even when an endoscope is introduced into the endotube for positioning thereof, so that the limbs can be easily passed through a constriction. The funnel-like enlargement portion (1) is such that it forms a non-rotatable connection together with an inserted positioning tube.

17 Claims, 2 Drawing Sheets

ENDOTUBE

The invention relates to an endotube for positioning in particular in the esophagus, comprising a tubular central portion, at one end thereof a funnel-like enlargement portion and at the other end a thickened portion which is enlarged towards the central portion and which after passing through a constriction prevents the endotube from being pulled back or makes it difficult for the endotube to be pulled back.

It is known when dealing with stenoses of the esophagus, which are caused for example by carcinomas, for endotube or a by-pass tube to be inserted after the bougie operation, that tube making it possible for the patient to continue to swallow solid and liquid foods. The operation of using a bougie on the stenoses and subsequently setting the endotubes in position is effected in known manner either under X-ray control or by viewing through an endoscope; in that case, in known manner, the endoscope is passed through a tubular opening in the bougie. In the same manner the endoscope may also be passed through the opening in the endotube, thus facilitating the operation of setting it in place. So that the endotube remains secured at its appropriate position after the operation of setting it in place, the front side of the endotube is either fixed by operation from the stomach, after it has been set in place, or the endotube is provided in known manner at its front end with a collar-like thickened portion which makes it difficult for it to be pulled back through the stenoses. At thie rear end, which is towards the mouth, the known endotubes are provided with funnel-like enlargement portions to match them to the anatomical circumstances and to secure them in position. Regarding the state of the art discussed, attention is directed for example to EP-A-No. 138,089. Further examples of endotubes are discussed in the "British Journal of Surgery", volume 69 (1982), pages 61 to 68, and also in "Endoscopy" 8 (1976), pages 180 to 185.

The object of the present invention is to improve the known endotubes to provide for easier positioning thereof, including when viewing through an endoscope, both in regard to their function and their handling.

To achieve that object, the present invention takes as its starting point an endotube of the kind set forth in the opening part of this specification, and is characterized in that the thickened portion comprises two or more hollow thin-walled limbs which are open to the interior of the central portion and which project out from the central portion and whose height rises in a ramp-like configuration towards the central portion and which then terminate with a steep drop. Unlike the known collar-like enlargement portions, the abovementioned limbs can be completely pressed or folded in, even when an endoscope is passed through the tube, so that no difficulties occur when the tube is introduced through a stenosis and set in place. After having passed through the stenosis, the limbs then fold out and then, by virtue of their steep drop which provides an action in the manner of a barb, prevent the tube from being pulled back.

Further developments of the invention are set forth in the subsidiary claims. Thus, advantageously, adjoining the steep drop portion of the limbs the central portion has flat portions which reduce the wall thickness of the central portion. That further facilitates the inward folding movement of the limbs, without increasing the diameter of the endotube. The bore of the tubular central portion is advantageously provided with inwardly projecting longitudinal beads or raised portions which may preferably also adjoin each other in such a way as to give a groove internal cross-section. That arrangement ensures that, in the event of subsequent bending of a tube which has been set in position in the esophagus, the tube is not completely closed off. A cross-section always remains between the bent-over longitudinal beads or raised portions, which is at least sufficiently large to permit saliva to flow therethrough and to enable liquid food to be swallowed.

A stiffening coil of plastic or steel wire may be embedded into the wall of the tubular central portion in known fashion. That increases the resistance of the tube to being compressed in the region of a stenosis. The funnel-like enlargement portion is advantageously oval in shape, to match it to the anatomical situation. If it should subsequently be necessary to remove an endotube again, that can be facilitated by virtue of the fact that embedded into the wall of the funnel-shaped enlargement portion is at least one barb which projects into the interior of the funnel-like enlargement portion. The endotube can then be engaged in a substantially better manner by engaging thread or wire into the hook. The hook can be bent from high-quality steel wire or it can be a stamped member made from high-quality steel plate or sheet.

The the purposes of inserting the endotubes according to the invention, a positioning tube is used in known manner; the positioning tube can also be pushed onto the endoscope going through the endotube and engages into the funnel-like enlargement portion, when pressure is applied. Recommended in conjunction therewith is a further development of the invention which provides that the funnel-like enlargement portion has inwardly projecting bead-like limb portions which form a nonrotatable connection, in conjunction with matching grooves at the foot of the positioning tube. The oval configuration of the funnel-like enlargement portion is generally not sufficient to prevent a rotary movement as between the endotube and the positioning tube. However the possibility of rotating the endotube by means of the positioning tube when fitting it into position frequently makes it easier to carry out the positioning operation. The hooks for pulling an endotube may advantageously be embedded into the inside wall of the funnel-like enlargement portion in the region of the bead-like limb portions. That is the location at which the hooks cause the least problem and in addition the larger wall thickness in the region of the bead-like limb portions facilitates the provision of an anchoring effect which is resistant to a pulling force. In order to facilitate making the connection between the endotube and the positioning tube, under X-ray control, a metal ring is desirably embedded into the end of the positioning tube. For the purposes of adaptation to the individual situation in each respective patient, in a further development of the invention, an additional or ancillary portion may be fitted onto the funnel-like enlargement portion in such a way as to adhere thereto. In that respect the ancillary portion is of such a configuration that it increases the thickness of and/or the length of the funnel-like enlargement portion.

Finally, in another embodiment of the invention, there is the possibility of fitting onto the tubular central portion at least one enlargement ring which is desirably of a thin and hollow configuration. It is possible for example to use such rings for covering over fistulae. So that the enlargement ring can bear snugly against the tube in the operation of setting it in place, with the air contained therein being sucked out or escaping, it is possible to provide that a tube can be passed into the hollow interior of the ring. Another possibility is for the wall of the tubular central portion to have a bore therethrough at the location of the enlargement ring.

The endotube as well as the ancillary portions and enlargement rings are advantageously made from silicone rubber of a suitable quality for medical purposes, or also other elastomers.

Figure 2:
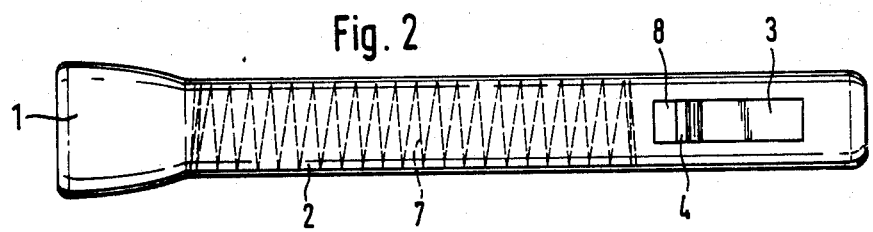
Figure 3:
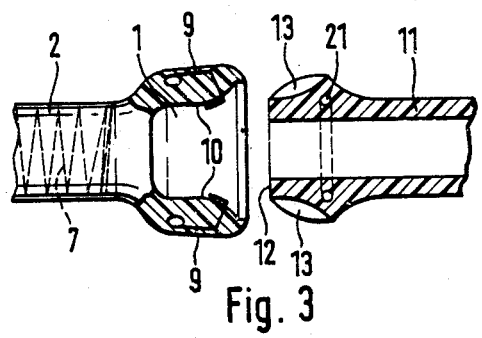
Figure 4:
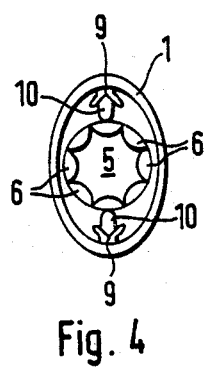
Figure 5:
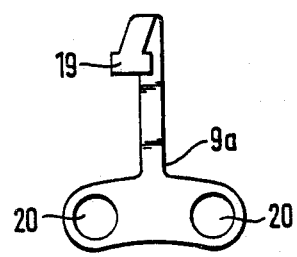
Figure 6:
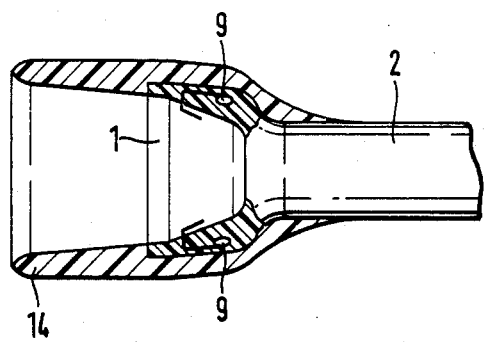
Figure 7:
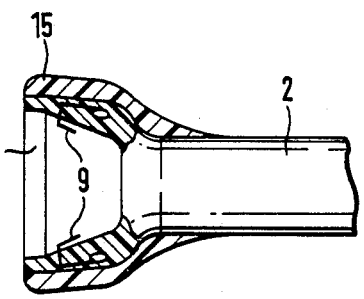
Figure 8:
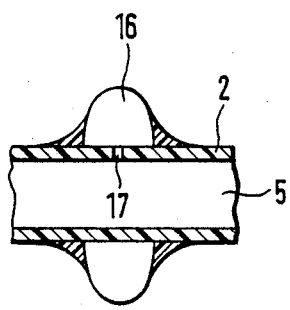

The invention is described hereinafter by means of embodiments with reference to the accompanying drawings in which:

FIG. 1 is a side view of an endotube according to the invention, in section in the front and rear regions thereof, FIG. 2 is a side view of the tube shown in FIG. 1 in a position of being turned through 90°, FIG. 3 shows th funnel-like enlargement portion of the endotube shown in FIGS. 1 and 2 with additional limb portions to provide rotation-preventing means as well as the head of an associated positioning tube prior to insertion thereof, FIG. 4 is an end view of the endotube shown in FIG. 3, viewing onto the funnel-like enlargement portion, FIG. 5 is a perspective view of a barb hook which is stamped out of high-quality steel sheet, FIGS. 6 and 7 are partly sectional side views of the endotube shown in FIGS. 1 and 2 with additional portions fitted thereon, and FIG. 8 shows a section of the central portion of an endotube according to the invention with an enlargement ring pushed thereon.

The endotube illustrated comprises, at the side which is on the left in the drawing, a funnel-like enlargement portion 1 of oval cross-section (see FIG. 4). Connected thereto is a tubular central portion 2 and disposed at the other end thereof on two mutually oppositely disposed sides are hollow thin-walled limbs 3 which are open to the interior and which rise in a ramp-like configuration and which have a steep drop at 4 on the rear side which is towards the central portion 2. Extending through the entir endotube is a bore 5 with which the endotube can be fitted onto an endoscope (not shown) for positioning thereof. The bore 5 has inwardly directed longitudinally bead or raised portions 6 (see FIG. 4), at least in the region of the central portion 2. The beads 6 generally provide a grooved cross-section. Even when the endotube is bent, there then still remains a flow cross-section for saliva and food which is of low viscosity. Embedded into the wall of the central portion 2 in per se known manner is a coil 7 of steel wire which produces a stiffening effect.

The hollow limbs 3 can be fully pressed or folded in, even when an endoscope is passed through the bore 5, so that the limbs 3 do not give rise ot any increase in diameter and the endotube can therefore be pushed through a stenosis and set in position, without any additional impediment. The folding-in movement of the limbs 3 is facilitated by a flat portion 8 on the central portion 2, adjoining the steeply sloping portion 4.

Embedded in the wall of the funnel-like enlargment portion are hooks 9 which are bent from steel wire and which project into the interior of the funnel-like portion. A thread or a wire (not shown) can then be engaged with the hook 9, to facilitate drawing a positioned tube. Instead of the hook 9 which is bent from wire, it is also possible to embed a barb hook 9a which is stamped out of high-quality steel sheet or plate, as shown separately in FIG. 5. In order to prevent the thread or wire used for pulling the endotube from slipping off, the hook 9a is provided at its free end with an enlargement portion 19. Anchoring of the hook 9a in the wall of the endotube is enhanced by bores 20.

In the modified embodiment shown in FIGS. 3 and 4, bead-like limb portions 10 project into the interior of the funnel-like enlargement portion 1. A positioning tube 11 which is shown in diagrammatic form in FIG. 3 has recesses 13 which match the limb portions 10, at its foot 12. When then the tube 11 is pressed into the funnel-like enlargement portion 1, that provides a non-rotary connection therebetween, just by virtue of the oval configuration of the enlargement portion 1 but additionally by means of the limb portions 10 and the grooves 13, so that the endotube can be turned by means of the positioning tube, in order to facilitate the positioning operation. The foot 12 of the positioning tube and the floor of the funnel-like enlargement portion 1 around the bore 5 are such as to provide contact over a large area which provides for the good transmission of force without however the endotube and the positioning tube becoming wedged or jammed together. After the positioning operation therefore the tube 11 can be easily pulled out of the funnel-like enlargement portion 1. In order to improve the embedding of the steel wire hooks, in such a way as to make them able to withstand a pulling force, the hooks are arranged in the region of the limb portions 10. Instead of the steel wire hooks 9, it would also be possible in this embodiment to use stamped hooks 9a as shown in FIG. 5. Embedded into the end of the tube 11 is an annular metal wire 21 which facilitates making the connection between the endotube and the positioning tube 11, under X-ray control.

FIGS. 6 and 7 show the endotube illustrated in FIGS. 1 and 2 in the region of the funnel-like enlargement portion 1, with a part of the tubular central portion 2 (with the stiffening coil 7 omitted), but with a supplementary or additional portion 14 and 15 respectively fitted onto the funnel-like enlargement portion in each of FIGS. 6 and 7. When the dimensions are correct and when alcohol is possibly used for moistening purposes, after the additional portion 14 or 15 has been fitted into position on the respective enlargement portion, the adhesion obtained is so good that it is practically no longer possible for the additional portion to be pulled off. The additional portion 15 provides for an increase in the size of the funnel-like enlargement portion 1 so that depending on the configuration of the additional portion 15, it is possible to provide for the desired effects in regard to matching the anatomical aspects of the patient concerned. An increase in the length of the endotube can be achieved in a similar manner with the additional portion 14. That is also important in particular for the purposes of covering over fistulae which occur on a large scale after laser irradiation operations.

FIG. 8 shows a section of the tubular central portion 2 of the endotube as shown in the preceding Figures, wherein the thin-walled enlargement ring 16 is pushed onto the central portion 2. The enlargement ring 16 makes it possible for example to cover over fistulae. It is also possible to use a plurality of rings of that kind, as required. So that the ring 16 can lie in snug contact when positioning the endotube, the wall of the central portion 2 is provided with a bore 17 at the respective location. In that case the air can escape from the ring 16 when it is compressed and can subsequently pass back into the ring again after the positioning operation. It is also possible for the same purpose to pass a thin tube or hose (not shown) into the enlargement ring 16, to make it possible to evacuate or inflate the ring.

What is claimed is:

1. A combination endotube and positioning tube, wherein said endotube comprises a substantially tubular central portion having first and second ends, a funnel-like enlargement portion at said first end thereof, and an enlarged end portion at said second end, which increases in its transverse dimension in a direction towards the central portion and which is adapted after passing through a constriction to safely resist the endotube being pulled back through said constriction, said enlarged end portion including at least two firm, hollow, thin-walled limb portions which are open to the interior of said central portion and which extend out of said central portion and which in longitudinal cross-section are of a ramp-like configuration rising in said direction towards said central portion and then terminating with a steeply dropping portion, said firm, hollow, thin-walled limb portions being fully yieldable to said constriction when moved therethrough and;

wherein said positioning tube in combination with said endotube is adapted to co-operate with said endotube for positioning same and includes connecting means adapted to provide a non-rotatable connection therebetween, said enlargement portion having therein inwardly projecting bead-like limb portions and wherein said connecting means of said positioning tube comprises grooves adapted to co-operate with said bead-like limb portions.

2. An endotube as set forth in claim 1 wherein the bore through said central portion has inwardly projecting longitudinal beads therein.

3. An endotube as set forth in claim 2 wherein said longitudinal beads are in adjoining relationship such as to provide a grooved internal cross-section in said bore.

4. An endotube as set forth in claim 1 and further including a stiffening coil embedded in the wall of said central portion.

5. An endotube as set forth in claim 1 wherein said enlargement portion is of an oval shape in cross-section.

6. An endotube as set forth in claim 5 further including at least one catching means fixed on an inner wall of said enlargement portion and extending into the interior thereof, adapted to permit the endotube to be pulled thereby.

7. An endotube as set forth in claim 6 wherein said catching means is a hook partially embedded in said wall.

8. An endotube as set forth in claim 7 wherein said hook is bent from high-quality steel wire.

9. An endotube as set forth in claim 7 wherein said hook is a stamped component of high-quality steel sheet.

10. An endotube as set forth in claim 1 wherein said enlargement portion is of an oval cross-section and said bead-like limb portions extend in mutually opposite relationship along respective generatrices in the region of which the inside surface of said enlargement portion is of its smallest radius of curvature.

11. An endotube as set forth in claim 1 further including at least one hook carried by the wall of said enlargement portion in the interior thereof in the region of said bead-like limb portions.

12. An endotube as set forth in claim 1 and further including an additional portion adapted to be fitted on to said enlargement portion in adhering relationship thereon, said additional portion providing for an increase in at least one of the dimensions of thickness and length of said enlargement portion.

13. An endotube as set forth in claim 1 and further comprising at least one firm enlargement ring adapted to be fitted on to said central portion thereby to increase the transverse dimension thereof.

14. An endotube as set forth in claim 13 wherein said enlargement ring is of a hollow thin-walled configuration.

15. An endotube as set forth in claim 14 wherein a conduit means provides a communication between the hollow interior of said ring and the interior of said central portion.

16. An endoscope as set forth in claim 14 and further including a conduit communicating with the interior of said ring for inflation and deflation thereof.

17. A combination as set forth in claim 1 and including a metal ring embedded in said positioning tube adjacent said connecting means.

* * * * *